US009855305B2

(12) United States Patent
Villamil Torres et al.

(10) Patent No.: US 9,855,305 B2
(45) Date of Patent: Jan. 2, 2018

(54) PHARMACEUTICAL COMPOSITION CONTAINING COMBINATIONS OF VITAMINS, MINERALS, PROBIOTICS, AND PREBIOTICS EFFECTIVE IN PREVENTING ADVERSE EFFECTS ASSOCIATED WITH THE USE OF PROTON-PUMP INHIBITORS

(71) Applicant: Companion Supplements, LLC, Sunrise, FL (US)

(72) Inventors: Julio César Villamil Torres, Bogota (CO); Camilo Rey Ferro, Sunrise, FL (US)

(73) Assignee: Companion Therapeutics LLC, Sunrise, FL (US)

( * ) Notice: Subject to any disclaimer, the term of this patent is extended or adjusted under 35 U.S.C. 154(b) by 0 days.

(21) Appl. No.: 15/083,570

(22) Filed: Mar. 29, 2016

(65) Prior Publication Data

US 2017/0281697 A1  Oct. 5, 2017

(51) Int. Cl.
| | |
|---|---|
| *A01N 45/00* | (2006.01) |
| *A61K 9/20* | (2006.01) |
| *A61K 35/747* | (2015.01) |
| *A61K 31/593* | (2006.01) |
| *A61K 31/122* | (2006.01) |
| *A61K 31/714* | (2006.01) |
| *A61K 33/06* | (2006.01) |
| *A61K 33/26* | (2006.01) |
| *A61K 31/7088* | (2006.01) |
| *A61K 38/28* | (2006.01) |

(52) U.S. Cl.
CPC .......... *A61K 35/747* (2013.01); *A61K 31/122* (2013.01); *A61K 31/593* (2013.01); *A61K 31/7088* (2013.01); *A61K 31/714* (2013.01); *A61K 33/06* (2013.01); *A61K 33/26* (2013.01); *A61K 38/28* (2013.01)

(58) Field of Classification Search
CPC .. A61K 35/747; A61K 31/593; A61K 31/714; A61K 33/06; A61K 31/122; A61K 33/26; A61K 9/20; A01N 45/00
USPC ............... 424/464, 465, 93.45; 514/167, 168
See application file for complete search history.

(56) References Cited

U.S. PATENT DOCUMENTS

| | | | |
|---|---|---|---|
| 5,571,441 A * | 11/1996 | Andon | A23L 33/16 252/1 |
| 6,790,462 B2 | 9/2004 | Hendricks | |
| 6,929,793 B2 | 8/2005 | Spivey-Krobath et al. | |
| 2004/0161422 A1* | 8/2004 | Ranganathan | A61K 9/1652 424/93.45 |
| 2005/0037089 A1 | 2/2005 | Jobbins | |
| 2005/0123603 A1 | 6/2005 | Dalland et al. | |
| 2008/0166423 A1 | 7/2008 | Sundharadas | |
| 2009/0117056 A1* | 5/2009 | Hodal, Jr. | A61K 9/2018 424/48 |
| 2010/0104696 A1 | 4/2010 | Banavara et al. | |
| 2014/0093613 A1 | 4/2014 | Cevallos et al. | |
| 2014/0161955 A1 | 6/2014 | Wadhwa | |
| 2014/0328932 A1 | 11/2014 | Mogna | |
| 2016/0015746 A1* | 1/2016 | Bortz | A23L 29/06 424/94.6 |

FOREIGN PATENT DOCUMENTS

| | | |
|---|---|---|
| WO | 2011018547 A1 | 2/2011 |
| WO | 2014149434 A1 | 9/2014 |
| WO | 2014152338 A1 | 9/2014 |
| WO | 2015084531 A1 | 6/2015 |

OTHER PUBLICATIONS

Larner, A.J. and Lendrum, R., Oesophageal candidiasis after omeprazole therapy, Gut 33:860-861 (1992).
FDA Consumer Health Information, Possible Increased Risk of Bone Fractures with Certain Antacid Drugs May 2000.
Goenka, Mahesh et al., Candida Overgrowth After Treatment of Duodenal Ulcer: A Comparison of Cimetidine, Famotidine, and Omeprazole, J. of Clinical Gastroenterology 23(1):7-10 (1996).
Khalili, H. et al., Use of proton pump inhibitors and risk of hip fracture in relation to dietary and lifestyle factors: a prospective cohort study, BMJ (Jan. 31, 2012).
Martinez, A. Chocarro et al., Risk Factors for Esophageal Candidiasis, Eur. J. Clin. Micribiol. Infect. Dis. 19:96-100 (2000).
PRILOSEC Label Dec. 2014.
Shimura, Shino, Diarrhea Caused by Proton Pump Inhibitor Administration: Comparisons Among Lansoprazole, Rabeprazole, and Omeprazole, Curr. Therap. Res. 73(3): 112-120 (2012).
Tetsuhide, Ito et al., Association of Long-term Proton Pump Inhibitor Therapy with Bone Fractures and effects on Absorption of Calcium, Vitamin B12, Iron, and Magnesium, Curr. Gastroenterol Rep. 12(6):448-457 (2010).
Vestergaard, P. et al., Proton Pump Inhibitors, Histamine H2 Receptor Antagonists, and Other Antacid Medications and the Risk of Fracture, Calcified Tissue International 79:76-83 (2006).
Yang, Yu-Xiao et al., Long-term Proton Pump Inhibitor Therapy and Risk of Hip Fracture, JAMA 296(24):2947-2954 (2007).
Gray, Shelly et al., Proton Pump Inhibitor Use, Hip Fracture, and Change in Bone Mineral Density in Postmenopausal Women, Arch. Intern. Med. 170(9)165-771 (2010).
ISR, PCT/US2017/024248.

\* cited by examiner

*Primary Examiner* — Scott Long
*Assistant Examiner* — Paul Martin
(74) *Attorney, Agent, or Firm* — The Morales Law Firm, LLC; Joseph L. Morales

(57) ABSTRACT

The present invention relates to a pharmaceutical composition containing a combination of vitamins, specific salts of calcium, magnesium, and iron, probiotics and prebiotics, which prevents the occurrence of adverse effects associated with long-term use of proton-pump inhibitors (PPIs). This effect is achieved by restoring all nutrient deficiencies and rectifying the intestinal flora imbalance caused by this type of drugs, particularly in patients with gastroesophageal reflux disease and Zollinger-Ellison syndrome.

23 Claims, 2 Drawing Sheets

PHARMACEUTICAL COMPOSITION CONTAINING COMBINATIONS OF VITAMINS, MINERALS, PROBIOTICS, AND PREBIOTICS EFFECTIVE IN PREVENTING ADVERSE EFFECTS ASSOCIATED WITH THE USE OF PROTON-PUMP INHIBITORS

FIELD OF THE INVENTION

The present invention relates to pharmaceutical compositions containing a combination of vitamins, minerals, probiotics and prebiotics, useful in the prevention of the adverse effects associated with long-term use of proton-pump inhibitors (PPIs).

BACKGROUND OF THE INVENTION

Proton-pump inhibitors (PPIs) are a class of drugs with a broad range of applications worldwide. Although they have shown a very favorable safety profile, nowadays its potential for adverse effects on long-term use has caused great interest, due to the fact that the number of patients who use these drugs chronically, especially in gastroesophageal reflux disease, has increased significantly.

PPIs work by blocking the body mechanism which secretes hydrochloric acid into the stomach, known as proton pump. By this action, the improvement of symptoms in patients suffering from gastroesophageal reflux, peptic ulcer, duodenal ulcer, erosive esophagitis and Zollinger-Ellison syndrome is achieved.

Nevertheless, hydrochloric acid in the stomach plays an important role in several biological processes, so its inhibition for long periods of time can cause undesirable side effects. This situation becomes critical in patients with gastroesophageal reflux disease and Zollinger-Ellison syndrome, because PPIs are used for a very long term in these conditions. In the case of Zollinger-Ellison in particular, the use of PPIs is a lifelong and high-dose therapy.

There are basically three functions of hydrochloric acid affected when its secretion is suppressed, which are the following:
1. Help break down food into smaller molecules for subsequent absorption;
2. Aid in the absorption of some nutrients; and
3. Prevent microbial proliferation by maintaining an acidic pH, which prevents the growth of microorganisms, especially the pathogenic ones.

When the secretion of hydrochloric acid stops for a long time due to the use of PPIs, the three referred functions are altered and situations such as those listed below begin to appear:

First, there are nutrients requiring the acidic environment generated by hydrochloric acid for their absorption (calcium being the most important one). In the absence of hydrochloric acid, calcium from food and even calcium salts commonly used in dietary supplements cannot dissolve and therefore cannot be absorbed properly. The long term consequence of this malabsorption is the increased incidence of osteoporosis-related fractures.

Something similar happens with magnesium. Malabsorption of magnesium for long periods of time, which is caused by continuous use of PPIs, can cause hypomagnesemia. The consequences of hypomagnesemia may include fatigue, tetany, unsteadiness, paresthesia, seizures and cardiac arrhythmias.

Other types of nutrients require hydrochloric acid to be released from food and then absorbed. This is the case of vitamin B12 and iron. In absence of hydrochloric acid, these two important nutrients cannot be transformed into their free absorbable forms, becoming non-bioavailable. Poor absorption of iron and vitamin B12 for long periods of time can bring different undesirable effects, including anemia.

Finally, the absence of hydrochloric acid during extended periods of time favors gastrointestinal tract colonization by opportunistic pathogenic bacteria. This situation leads to events of diarrhea, esophageal candidiasis, and proliferation of *Helicobacter pylori*.

From the above, it is clear that there is a need to develop a product that comprehensively replenishes all nutrient deficiencies, as well as the imbalance of the intestinal flora, caused by prolonged use of PPIs. This product should be formulated from usable components in achlorhydria (absence of hydrochloric acid) or hypochlorhydria (low amount of hydrochloric acid) found in patients under treatment with PPIs.

In this regard, if nutritional deficiencies could be supplemented and gastrointestinal flora imbalance could be corrected, the adverse effects derived from them would no arise.

In the field of patents, there EP 0904784 A1 discloses a nutritional preparation designed especially for preventing and treating gastrointestinal tract disorders, comprising viable cells of each of the following microorganisms: *Enterococcus faecium, Bifidobacterium* and a *Lactobacillus* strain that produces predominantly dextro-rotary lactate. The nutritional preparation may further comprise a number of cells of a *Lactococcus* strain or *Micrococcus* strain. Besides, the preparation preferably contains prebiotic compounds and substances that inhibit bacterial adherence to the gastrointestinal tract wall. The preparation may be in the form of a food supplement, a ready-to-use nutritional composition, an infant formula or a tube feeding.

Patent EP 1917969 A1 discloses compositions containing probiotic strains, prebiotics, vitamin complexes with oligo-elements, lycopene, glutathione and possibly bioflavonoids, designed to avoid depletion of the intestinal flora and damage to organs after antibiotic treatment.

Patent application US 2012/0028914 discloses a pharmaceutical composition including PPIs and prebiotics for the comprehensive treatment of ulcer disease associated with infection by *Helicobacter pylori*. It discloses a pharmaceutical combination of a PPI and prebiotics to stimulate growth of lactobacilli in the upper sections of the gastrointestinal tract, including the duodenum, to significantly increase growth of lactobacilli which antagonize *Helicobacter pylori*.

SUMMARY OF THE INVENTION

The present invention provides a solution to the above and other problems by enabling a pharmaceutical composition that prevents adverse effects associated with the use of proton-pump inhibitors. A first object of the invention relates to a pharmaceutical formulation comprising mixtures of vitamin D3 (as cholecalciferol), vitamin K2 (as menaquinone-7), vitamin B12 (as methylcobalamin), calcium (as calcium citrate malate), magnesium (as magnesium oxide), iron (as ferrous bisglycinate), *Lactobacillus acidophilus, Lactobacillus casei*, FOS (fructooligosaccharides) and inulin.

In addition, the present invention discloses the method of preparation of the pharmaceutical composition and its use as part of a method of treatment to avoid adverse effects associated with the use of proton-pump inhibitors.

The above described objects of the invention, as well as any additional object that might arise, will be presented in detail and with adequacy in the section named "Detailed Description of the Invention", which will be the basis of the claims.

DESCRIPTION OF DRAWINGS

The above and other features, aspects, and advantages of the present invention are considered in more detail, in relation to the following description of embodiments thereof shown in the accompanying drawings, in which.

DETAILED DESCRIPTION OF THE INVENTION

Figure 1:
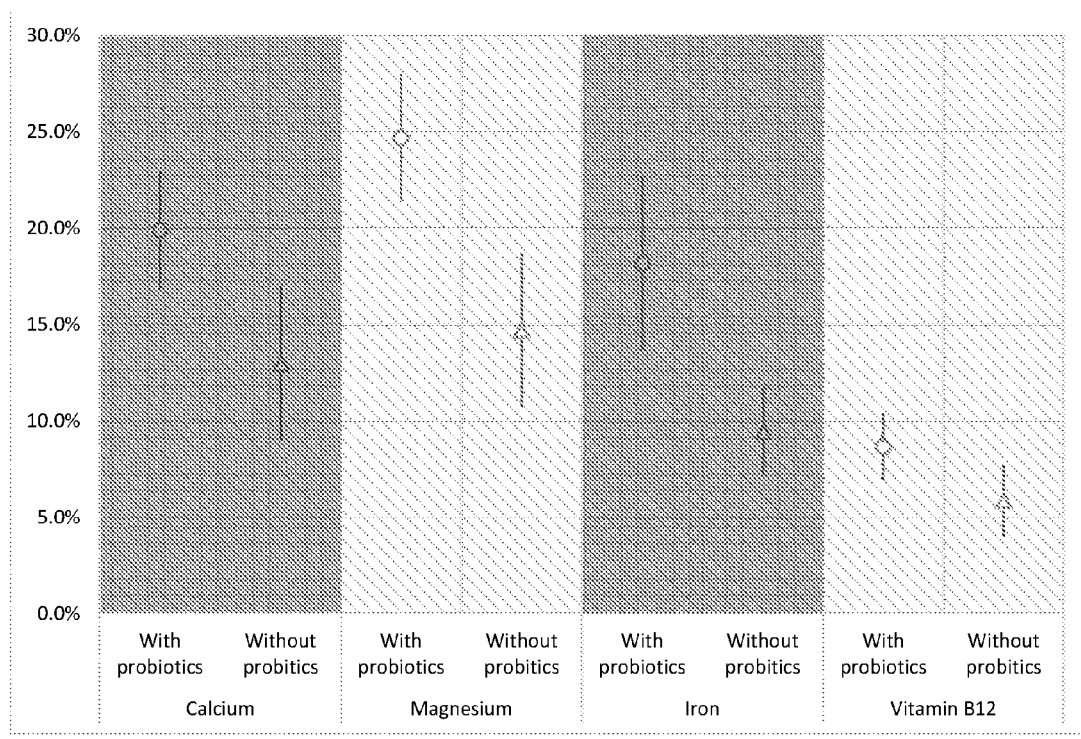
FIG. 1. Comparative absorption percentage of each element contained in the pharmaceutical formulation, when tested in a Franz cell system using pig intestine as the membrane.

The invention summarized above and defined by the enumerated claims may be better understood by referring to the following description, which should be read in conjunction with the accompanying drawings. This description of an embodiment, set out below to enable one to build and use an implementation of the invention, is not intended to limit the invention, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

Prior to the detailed description of the invention, definitions of some terms will be described.

The term "comprising" should be understood as not limiting. For the expected purposes of the present invention, the term "containing" is considered preferred to the term "composed of". If hereinafter a group is defined as comprising a number of embodiments, it is intended to encompass a group consisting of such embodiments preferably. The use of the letter "a" in claim elements does not limit the element to a single component, includes the use of multiple numbers of the element.

In general terms, a "pharmaceutical dosage" will be understood as formulation comprising an active ingredient in a specific amount in order to achieve a specific result.

The term "bioavailable", as exposed in the present invention, refers to the measurement of the amount and speed with which an active ingredient contained in a pharmaceutical preparation reaches the general circulation and becomes available at the site of action.

The term "probiotic" refers to live bacteria that replace or add to the beneficial bacteria normally present in the gastrointestinal tract, e.g. *Lactobacillus* or *Bifidobacterium*.

The term "prebiotic" refers to a nondigestible food ingredient that beneficially affects the host by selectively stimulating the growth and/or activity of one or a limited number of bacteria in the colon, and thus improves host health.

The term "Proton-pump inhibitors" or "PPIs" refers to a group of drugs whose main action is a pronounced and long-lasting reduction of gastric acid production.

The term "absorption ready" means a form of a compound, e.g., a mineral or a vitamin, whose absorption does not require hydrolysis, or other hydrochloric acid-mediated processes in the stomach. Such compounds can be absorbed in the achlorhydria or hypochlorhydria conditions in a human stomach.

The present invention discloses a novel pharmaceutical formulation, which is a supplement for all nutrient deficiencies, as well as a restorative element of the imbalance of the intestinal flora, which have been altered by prolonged use of PPIs in the treatment of gastrointestinal disorders.

The present invention arises as a response to the need to address the different effects suffered by patients facing the treatments of gastroesophageal reflux disease and Zollinger-Ellison syndrome, which in turn are caused by nutrient deficiencies and intestinal flora imbalance resulting from the prolonged use of proton-pump inhibitors (PPIs), on which the referred treatments are based.

The novel formulation and the pharmaceutical dosage form, referred in the present invention, were designed from components which are all usable in achlorhydria (absence of hydrochloric acid) or hypochlorhydria (low amount of hydrochloric acid) conditions, which are present in a patient being treated with PPIs.

The present invention discloses a novel pharmaceutical dosage for use in the prevention of side effects resulting from prolonged treatments with PPIs by means of a pharmaceutical preparation containing a mixture of vitamins, minerals, probiotics, and prebiotics in appropriate proportions to restore all nutrient deficiencies and the imbalance of intestinal flora caused by treatments with PPIs.

The species, forms or salts of each of the product components were carefully selected in order to ensure that they are absorbed and become bioavailable, even where there is no hydrochloric acid, as it happens in patients taking PPIs.

In one preferred embodiment, a pharmaceutical composition comprises a formulation containing calcium citrate malate, which is a type of calcium salt with a high solubility, even at a pH close to neutral, such as that observed in the stomach during a long treatment with PPIs. The foregoing makes its absorption into the body to be independent of the pH level and, thereby, ensures that calcium deficiencies could be overcome even in patients having a very low amounts of stomach hydrochloric acid or complete absence of hydrochloric acid.

During normal digestion, calcium has to be released from the complex in which it is found in food and transformed into its ionized form in order to be absorbed and utilized by the body. This process is facilitated, in part, by hydrochloric acid. When there is little or no acid (hypochlorhydria or achlorhydria), calcium cannot be released from the food and cannot be ionized. Therefore, calcium under these conditions cannot be absorbed.

When this situation remains for long periods, calcium stops reaching bones and osteoporosis occurs. Such lack of calcium ultimately results in an increased incidence of fractures, especially of the hip, wrist, and spine. Even calcium from most supplements is difficult to absorb because it also requires acid for ionization and subsequent absorption; therefore, not any calcium supplement can be useful when hydrochloric acid secretion is inhibited.

This information has been thoroughly verified, to the extent that the Food and Drug Administration (FDA) issued a warning indicating that long-term use of PPIs may cause this problem.

In the FDA document "highlights of prescribing information" for omeprazole, and in general for all PPIs marketed in the United States, a warning about this problem appears in the following terms: "Bone Fracture: Long-term and multiple daily dose PPI therapy may be associated with an increased risk for osteoporosis-related fractures of the hip, wrist or spine."

To this end, a comparative solubility study was conducted with different calcium salts at a physiological pH that could be found in the stomach and the upper part of the intestine in patients treated with PPIs.

This study was performed according to the USP guidelines for determining solubility, and consisted of the following stages:

1. Four pH values, representative of the pH range that can be found in the stomach and the upper part of the intestine in patients treated with PPIs were selected.
2. In addition to calcium citrate malate, four (4) of the most commonly used calcium salts in dietary supplements in the United States were selected: phosphate, citrate, malate, and carbonate salts.
3. Buffer solutions at the relevant pH were prepared as follows:
   a. Buffer at pH 2: 250 mL of 0.2 M potassium chloride+65.0 mL of 0.2 M hydrochloric acid solution, making 1 L volume with water.
   b. Buffer at pH 3: 250 mL of 0.2 M potassium hydrogen phthalate+111.5 mL of 0.2 M hydrochloric acid solution, making 1 L volume with water.
   c. Buffer at pH 4: 250 mL of 0.2 M potassium hydrogen phthalate+0.5 mL of 0.2 M hydrochloric acid solution, making 1 L volume with water.
   d. Buffer at pH 7: 250 mL of 0.2 M monobasic potassium phosphate+145.5 mL of 0.2 M sodium hydroxide, making 1 L volume with water
4. In five separate 50 mL Erlenmeyer flasks, aliquots of the buffer solution at pH 2 were placed. Subsequently, an excess of the five (5) study salts were placed in each Erlenmeyer flask, and were left under mechanical stirring at a 25° C. controlled temperature for 24 hours.
5. After 24 hours, the supernatant solution was filtered and the calcium content analyzed by volumetric titration with EDTA solution.
6. The process described in the previous numerals 4 and 5 was repeated two additional times, in order to obtain a total of three replicates of each test.
7. Finally, the processes described in numerals 4, 5, and 6 were repeated using the remaining three buffer solutions (Buffers at pH 3, pH 4 and pH 7).

The calcium citrate malate was the only salt maintaining its high solubility throughout the gastric pH range found in patients under PPI treatment. The solubility of the other calcium salts decreased as the pH increased, which is definitively detrimental to the absorption. Additionally, the calcium citrate malate was the salt which showed greater values throughout the pH range studied, in comparison to the other salts used in the test.

Using the appropriate form of calcium for achlorhydria or hypochlorhydria conditions is sufficient to ensure that this element will be absorbed from the digestive tract into the general circulation in patients with prolonged PPI treatment; however, this fact does not ensure that calcium will bind to bones, which is where it ultimately must exert its action. To this end, the present invention contains appropriate amounts of vitamin D3 and vitamin K2, which have proven to be important cofactors necessary for binding calcium into the bone tissue.

A similar situation occurs with magnesium. The long-term use of PPIs causes hypomagnesemia (low magnesium levels in the blood), which leads to fatigue, tetany, unsteadiness, paresthesia, seizures and cardiac arrhythmias.

In the FDA document "highlights of prescribing information" for omeprazole, and in general for all PPIs marketed in the United States, a warning about this problem also appears in the following terms: "Hypomagnesemia, symptomatic and asymptomatic, has been reported rarely in patients treated with PPIs for at least three months, in most cases after a year of therapy. Serious adverse events include tetany, arrhythmias, and seizures. In most patients, treatment of hypomagnesemia required magnesium replacement and discontinuation of the PPI."

In order to overcome the said deficiency, the present invention discloses a pharmaceutical formulation containing magnesium as magnesium oxide.

On the other hand, iron absorption is also affected by the lack of hydrochloric acid for prolonged periods. Gastric acid helps the iron containing food sources to dissociate the iron salts, helps to solubilize the iron salts which allows them to be reduced to the ferrous state, which allows the formation of complexes with ascorbate, sugars and amines which in term, facilitates absorption.

Iron malabsorption due to prolonged use of PPIs has been widely documented, and when this situation occurs for prolonged periods can lead to anemia. Iron present in food and in most dietary supplements requires hydrochloric acid for absorption. Gastric acid helps iron salts to dissociate and reduce, and subsequently form complexes with amino acids, which pass into the small intestine and are more easily absorbed. In the absence of gastric acid, this process cannot take place, and iron is removed from the gastrointestinal tract without the possibility of being absorbed and utilized by the body.

In the FDA document "highlights of prescribing information" for omeprazole, and in general for all PPIs marketed in the United States, there is also a warning about this problem in the following terms: "May interfere with drugs for which gastric pH affects bioavailability (e.g., ketoconazole, iron salts, erlotinib, ampicillin esters, digoxin and mycophenolate mofetil)"

For this purpose, the present invention discloses a pharmaceutical formulation containing a special source of absorption ready iron, in which the iron atom is in the reduced form and bound to an amino acid (glycine), which makes this important nutrient bioavailable and absorbable without the need of chemical processes which other types of iron require prior to their absorption, processes that are mediated by hydrochloric acid.

On the other hand, Vitamin B12 is an essential nutrient that must be acquired from the diet, is present in foods bound to protein, and the presence of gastric acid is needed for the peptic enzymes, and especially pepsin, to cleave the vitamin B12 from the protein, allowing its reassociation with intrinsic factor (IF) and eventual absorption in the terminal ileum.

In situations of lack or reduction of hydrochloric acid, the cleaving process of vitamin B12 from food cannot be carried out, leading to shortcomings in absorption. When this happens for extended periods of time, nerve damage and anemia may occur.

In the FDA document "highlights of prescribing information" for omeprazole, and in general for all PPIs marketed in the United States, this side effect is stated as follows: "Cyanocobalamin (vitamin B12) Deficiency: Daily long-term use (e.g., longer than 3 years) may lead to malabsorption or a deficiency of cyanocobalamin."

Vitamin B12 contained in the formulation is an absorption ready free-form vitamin that is not bound to proteins as in the case of food, so its absorption does not require hydrochloric acid to take place.

Besides the malabsorption of these four major nutrients, lack of hydrochloric acid caused by prolonged use of PPIs leads to another problem. Taking into account that another function of hydrochloric acid is to prevent microbial growth in the stomach, especially by opportunistic pathogenic microorganisms, lack of acid can promote gastrointestinal tract colonization by pathogenic bacteria.

There have been reported especially three types of infections caused by such bacteria:

1. Colonization of *Clostridium difficile* causing diarrhea, a well-known side effect of PPIs. In the FDA document "highlights of prescribing information" for omeprazole, and in general for all PPIs marketed in the United States, the following is stated: "Published observational studies suggest that PPI therapy may be associated with an increased risk of *Clostridium difficile* associated diarrhea, especially in hospitalized patients. This diagnosis should be considered for diarrhea that does not improve."
2. *Candida* spp. can also colonize the esophagus in patients taking PPIs for long periods of time, leading to esophageal candidiasis. LARNER, A. J., LENDRUM, R. Esophageal candidiasis after omeprazole therapy./ CHOCARRO, A. et al. Risk Factors for Esophageal Candidiasis./GOENKA, M. K. et al. *Candida* Overgrowth after Treatment of Duodenal Ulcer: A Comparison of Cimetidine, Famotidine, and Omeprazole.
3. The colonization of the stomach by *Helicobacter pylori* is definitely a concern after a long-term use of PPIs, since colonization may cause atrophic gastritis, a risk factor for the development of adenocarcinoma. The FDA document "highlights of prescribing information" for omeprazole, and in general for all PPIs marketed in the United States, states the following: "Atrophic gastritis: has been noted with long-term therapy."

Finally, in a specifically preferred embodiment of the invention, a pharmaceutical dosage form features probiotics which, through a competition mechanism, prevent pathogens such as *Clostridium difficile, Candida* spp., and *Helicobacter pylori* from proliferating into the body of patients with abnormal levels hydrochloric acid due to a treatment using PPIs for prolonged periods. In one preferred embodiment, the probiotic comprises a mixture 50:50 comprising *Lactobacillus acidophilus* and *Lactobacillus casei*.

The pharmaceutical preparation which is the object of the present invention is designed to be administered as a daily dose of one single stick pack or sachet, or two tablets or capsules, or one tablet and one capsule to be taken simultaneously.

In a preferred embodiment of the invention, the pharmaceutical dosage includes a stick pack or sachet packaging containing the total amount of a daily dose plus a flavored base, as can be seen in the following Table (Table 1).

TABLE 1

Pharmaceutical dosage including a stick pack or sachet packaging containing the total daily dose

| Component | Daily dose | Amount per sachet |
|---|---|---|
| Calcium (as calcium citrate malate) | Between 200 mg and 1,000 mg | Between 200 mg and 1,000 mg |
| Vitamin D3 (as cholecalciferol) | Between 200 IU and 1,000 IU | Between 200 IU and 1,000 IU |
| Vitamin K2 (as menaquinone-7) | Between 25 µg and 200 µg | Between 25 µg and 200 µg |
| Magnesium (as magnesium oxide) | Between 50 mg and 500 mg | Between 50 mg and 500 mg |
| Iron | Between 6 mg and | Between 6 mg and |

TABLE 1-continued

Pharmaceutical dosage including a stick pack or sachet packaging containing the total daily dose

| Component | Daily dose | Amount per sachet |
|---|---|---|
| (as ferrous bisglycinate) | 90 mg | 90 mg |
| Vitamin B12 (as methylcobalamin) | Between 6 µg and 250 µg | Between 6 µg and 250 µg |
| Lactobacillus acidophilus | Between 1 and 10 billion CFU | Between 1 and 10 billion CFU |
| Lactobacillus casei | Between 1 and 10 billion CFU | Between 1 and 10 billion CFU |
| FOS (fructooligosaccharides) | Between 25 mg and 500 mg | Between 25 mg and 500 mg |
| Inulin | Between 25 mg and 500 mg | Between 25 mg and 500 mg |

In another preferred embodiment of the invention, the pharmaceutical dosage comprises two capsules or two tablets, each capsule or tablet containing 50% of the dose of each component, as it can be seen in the following Table (Table 2):

TABLE 2

Pharmaceutical dosage comprising two capsules or two tablets

| Component | Daily dose | Amount per capsule/tablet |
|---|---|---|
| Calcium (as calcium citrate malate) | Between 200 mg and 1,000 mg | Between 100 mg and 500 mg |
| Vitamin D3 (as cholecalciferol) | Between 200 IU and 1,000 IU | Between 100 IU and 500 IU |
| Vitamin K2 (as menaquinone-7) | Between 25 µg and 200 µg | Between 12.5 µg and 100 µg |
| Magnesium (as magnesium oxide) | Between 50 mg and 500 mg | Between 25 mg and 250 mg |
| Iron (as ferrous bisglycinate) | Between 6 mg and 90 mg | Between 3 mg and 45 mg |
| Vitamin B12 (as methylcobalamin) | Between 6 µg and 250 µg | Between 3 µg and 125 µg |
| Lactobacillus acidophilus | Between 1 and 10 billion CFU | Between 0.5 and 5 billion CFU |
| Lactobacillus casei | Between 1 and 10 billion CFU | Between 0.5 and 5 billion CFU |
| FOS (fructooligosaccharides) | Between 25 mg and 500 mg | Between 12.5 mg and 250 mg |
| Inulin | Between 25 mg and 500 mg | Between 12.5 mg and 250 mg |

In another preferred embodiment of the invention, the pharmaceutical dosage includes two capsules or tablets with possible different compositions, but in any case, intended to be swallowed simultaneously. These two capsules or tablets would be in a package (double blister), with the two tablets, the two capsules or the combination of one capsule and one tablet included in a single compartment. The compositions are given in the following Tables (Table 3.1. and Table 3.2):

TABLE 3.1

Composition per capsule or tablet 1

| Component | Amount per capsule/tablet |
|---|---|
| Calcium (as calcium citrate malate) | Between 136 mg and 680 mg |
| Lactobacillus acidophilus | Between 1 and 10 billion CFU |
| Lactobacillus casei | Between 1 and 10 billion CFU |
| FOS (fructooligosaccharides) | Between 25 mg and 500 mg |

TABLE 3.1-continued

Composition per capsule or tablet 1

| Component | Amount per capsule/tablet |
|---|---|
| Inulin | Between 25 mg and 500 mg |

TABLE 3.2

Composition per capsule or tablet 2

| Component | Quantity per capsule/tablet |
|---|---|
| Calcium (as calcium citrate malate) | Between 64 mg and 320 mg |
| Vitamin D3 (as cholecalciferol) | Between 200 IU and 1,000 IU |
| Vitamin K2 (as menaquinone-7) | Between 25 µg and 200 µg |
| Magnesium (as magnesium oxide) | Between 50 mg and 500 mg |
| Iron (as ferrous bisglycinate) | Between 6 mg and 90 mg |
| Vitamin B12 (as methylcobalamin) | Between 6 µg and 250 µg |

The preferred embodiment of the invention is a pharmaceutical dosage form containing an amount of calcium, expressed as a daily dose of elemental calcium, which may vary from 200 mg to 1,000 mg, preferably between 250 mg and 500 mg.

The preferred embodiment of the invention is a pharmaceutical dosage form containing an amount of vitamin D3, expressed as a daily dose, which may vary between 200 IU and 1,000 IU, preferably between 400 IU and 800 IU.

The preferred embodiment of the invention is a pharmaceutical dosage form containing an amount of vitamin K2, expressed as a daily dose, which may vary between 25 mg and 200 mg, preferably between 50 mg and 100 mg The preferred embodiment of the invention is a pharmaceutical dosage form containing an amount of magnesium, expressed as a daily dose of elemental magnesium, which may vary between 50 mg and 500 mg, preferably between 100 mg and 400 mg.

The preferred embodiment of the invention is a pharmaceutical dosage form containing an amount of iron, expressed as a daily dose of elemental iron, which may vary between 6 mg and 90 mg, preferably between 18 mg and 45 mg.

The preferred embodiment of the invention is a pharmaceutical dosage form containing an amount of vitamin B12, expressed as a daily dose, which may vary between 6 mg and 250 mg; preferably between 50 mg and 100 mg.

The preferred embodiment of the invention is a pharmaceutical dosage form containing an amount of *Lactobacillus acidophilus*, expressed as a daily dose, which may vary between 1 billion and 10 billion CFU, preferably between 2.5 billion and 7.5 billion CFU.

The preferred embodiment of the invention contains an amount of *Lactobacillus casei*, expressed as a daily dose, which may vary between 1 billion and 10 billion CFU, preferably between 2.5 billion and 7.5 billion CFU.

The preferred embodiment of the invention contains an amount of fructooligosaccharides, expressed as a daily dose, which may vary between 25 mg and 500 mg, preferably between 50 mg and 200 mg.

The preferred embodiment of the invention contains an amount of inulin, expressed as daily dose, which may vary between 25 mg and 500 mg, preferably between 50 mg and 200 mg.

Further embodiments of the invention comprise the modifications listed below:

In the preferred embodiment of the invention, the preferred calcium source is calcium citrate malate, but calcium citrate, calcium carbonate, calcium ascorbate, calcium chelates or aminochelates, calcium gluconate, calcium malate, calcium glycinate, calcium aspartate, calcium succinate, calcium fumarate, or mixtures thereof can be used.

In the preferred embodiment of the invention, the preferred form of vitamin D3 is cholecalciferol, but calciferol, ergocalciferol or mixtures thereof can be used.

In the preferred embodiment of the invention, the preferred form of vitamin K2 is menaquinone-7, but menaquinone-4, or mixtures thereof can be used.

In the preferred embodiment of the invention, the preferred form of magnesium is magnesium oxide, but magnesium citrate, magnesium malate, magnesium amino chelate, magnesium glycinate, magnesium carbonate, or mixtures thereof can be used.

In the preferred embodiment of the invention, the preferred form of iron salt is ferrous bisglycinate, but heme iron polypeptide, ferrous sulfate, ferrous fumarate, iron glycinate, iron pyrophosphate or mixtures thereof can be used.

In the preferred embodiment of the invention, the preferred form of vitamin B12 is the methylcobalamin, but cyanocobalamin, hydroxocobalamin or mixtures thereof can be used.

In relation to the mixture of probiotics in the specifically preferred embodiment of the invention, those probiotics preferred are *Lactobacillus acidophilus* and *Lactobacillus casei*, but *Bacillus clausi, Bacillus coagulans, Lactobacillus brevis, Lactobacillus vulgaricus, Lactobacillus rhamnosus, Lactobacillus helveticus, Lactobacillus lactis, Lactobacillus reuteri, Bifidobacterium bifidum, Streptococcus thermophiles*, or *Enterococcus faecium* can also be used.

In addition to using chemical forms favoring the utilization of the four nutrients whose absorption is affected by prolonged use of PPIs, it was shown that the inclusion of probiotics in the preparation significantly favors the absorption of these nutrients, even in hypochlorhydria or achlorhydria conditions, giving probiotics a dual role in the present invention.

First of all, they prevent the proliferation of pathogenic microorganisms in a gastrointestinal tract devoid of an acidic environment for its protection, and secondly, they promote the absorption of the nutrients that the preparation intends to supplement and whose utilization is limited by achlorhydria or hypochlorhydria conditions in which patients under long-term treatment with PPIs are immersed.

The foregoing was evident in a laboratory test described in Example 2, which shows the differential absorption of the four relevant nutrients in a medium prepared at pH 6, simulating the condition of achlorhydria, both with and without probiotics.

In a preferred embodiment, the pharmaceutical composition of the present invention is administered during all the time that the patient is being treated with the proton-pump inhibitor (PPI). The administration is performed once a day, with food, between four and six hours after the PPI. The total amount of a daily dose is given in the form of a single sachet or stick pack, or two tablets or capsules, or one tablet and one capsule to be taken simultaneously.

In another preferred embodiment, the pharmaceutical composition of the present invention is administered during all the time that the patient is being treated with the proton-pump inhibitor (PPI). The administration is performed twice a day; the first administration is performed with food, between four and six hours after the PPI, while the second administration is performed with food, between 6 and 8 hours after the first administration. In this case, the total amount of the daily dose is divided in each of the two administrations, in the form of a capsule or tablet, each one containing 50% of the dose of each component.

In one preferred embodiment, the pharmaceutical composition comprises a) cholecalciferol from 5 μg and 10 μg, equivalent to 200 IU to 400 IU of vitamin D3; b) menaquinone-7 from 25 μg to 50 μg; c) methylcobalamin from 25 μg to 50 μg; d) calcium citrate malate from 523 mg to 1,046 mg, equivalent to 125 mg to 250 mg of elemental calcium; e) magnesium oxide from 83 mg to 332 mg, equivalent to 50 mg to 200 mg of elemental magnesium; f) ferrous bisglycinate from 45 mg to 112.5 mg, equivalent to 9 mg to 22.5 mg of elemental iron; g) *Lactobacillus acidophilus* from 1.25 to 3.75 billion CFU; h) *Lactobacillus casei* from 1.25 to 3.75 billion CFU; i) FOS (fructooligosaccharides) from 25 mg to 100 mg; and j) inulin from 25 mg to 100 mg.

Example 1

A sample of 2,000 capsules using the preferred formulation, which is described in the following Table (Table 4), was prepared.

TABLE 4

Sample of 2,000 capsules using the preferred formulation

| Component | Amount per capsule | Amount per 2,000 capsules |
|---|---|---|
| Calcium citrate malate | 523 mg | 1,048.0 g |
| Vitamin D3 | 10 μg | 0.02 g |
| Vitamin K2 | 50 μg | 0.10 g |
| Magnesium oxide | 83 mg | 166.0 g |
| Iron bisglycinate | 45 mg | 90.0 g |
| Vitamin B12 | 50 μg | 0.10 g |
| *Lactobacillus acidophilus* | 2.5 billion CFU, 4.2 mg | 8.4 g |
| *Lactobacillus casei* | 2.5 billion CFU, 4.2 mg | 8.4 g |
| FOS (fructooligosaccharides) | 25 mg | 50.0 g |
| Inulin | 25 mg | 50.0 g |

Excipients for 2,000 capsules: Microcrystalline cellulose, 210.98 g; Sodium croscarmellose, 34 g; Colloidal silicon dioxide, 17 g; Vegetable magnesium stearate, 17 g. The capsule was "#00" elongated.

Figure 2:
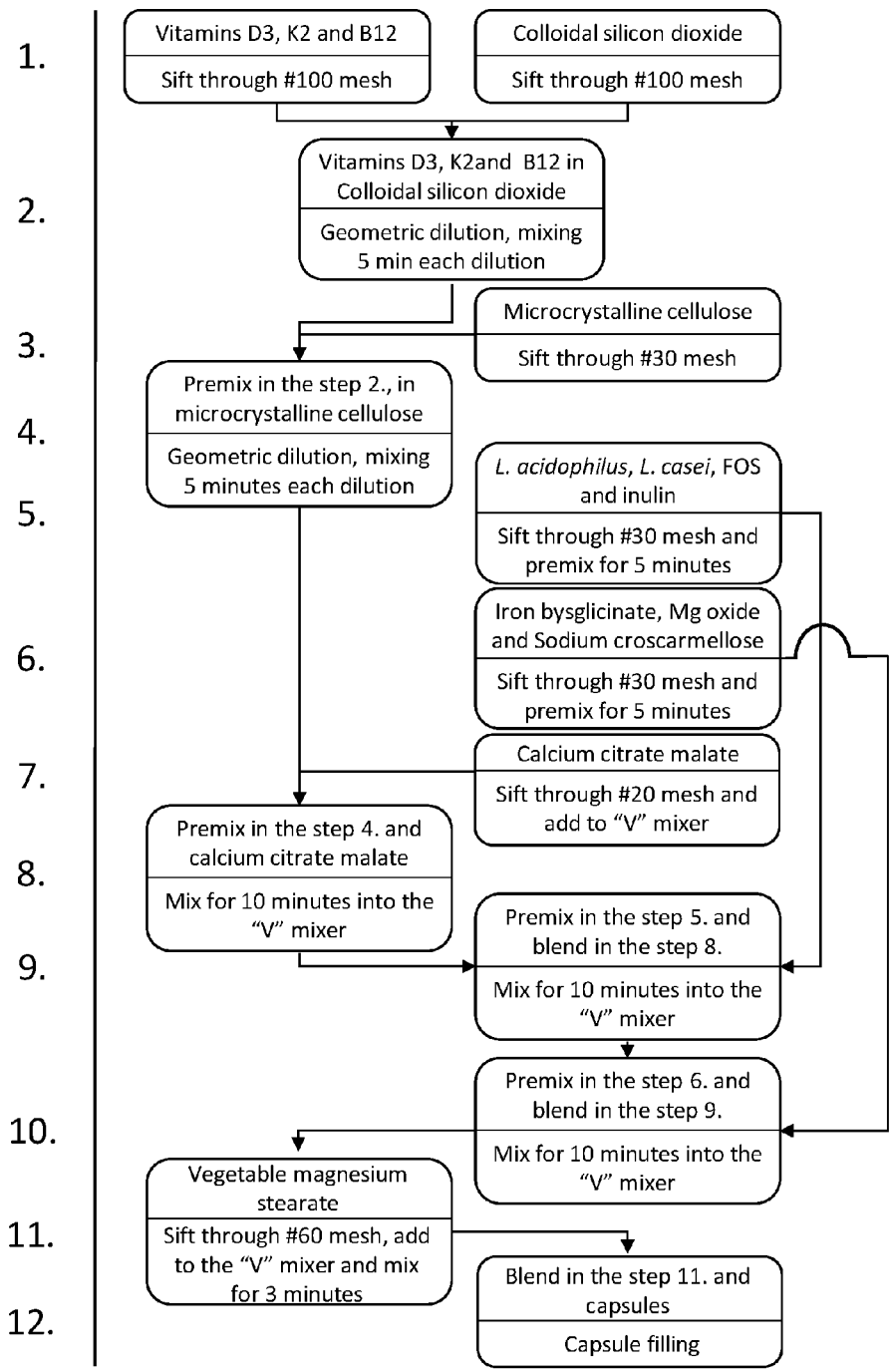
FIG. 2. A flow diagram for a method for preparation of a formulation according to one embodiment of the present invention.

The preferred formulation described in Table 4 was prepared by the following method, as shown in FIG. 2:
1. Vitamins D3, K2, and B12, and colloidal silicon dioxide were sifted through a #100 mesh.
2. Then, vitamins D3, K2, and B12 were geometrically diluted in colloidal silicon dioxide, mixing for 5 minutes at each dilution.
3. Microcrystalline cellulose was sifted through a #30 mesh.
4. The geometric dilution of the pre-mix obtained in step 2 in microcrystalline cellulose was carried out, mixing for 5 minutes at each dilution.
5. Separately, *Lactobacillus acidophilus*, *Lactobacillus casei*, FOS (fructooligosaccharides), and inulin were mixed for 5 minutes after being previously sifted through a #30 mesh.
6. Separately, iron bisglycinate, magnesium oxide, and sodium croscarmellose were mixed for 5 minutes after being previously sifted through a #30 mesh.
7. The total amount of calcium citrate malate was placed in a "V" mixer after being previously sifted through a #20 mesh.
8. The pre-mix obtained in step 4 was added to the mixer and mixed for 10 minutes.
9. The pre-mix obtained in step 5 was added to the mixer and mixed for 10 minutes.
10. The pre-mix obtained in step 6 was added to the mixer and mixed for 10 minutes.
11. The vegetable magnesium stearate, previously sifted through a #60 mesh, was added to the mixer and mixed for 3 minutes.
12. The "#00" elongated capsule was filled to obtain an average weight of 850 mg per capsule.

Example 2

A study was conducted to evaluate the potential effect of probiotics in the absorption of calcium, magnesium, iron, and vitamin B12, which are the four nutrients whose utilization is diminished in patients taking PPIs for long periods of time.

This study simulated the condition of achlorhydria, which is expected in patients under treatment with this type of drugs.

For the study, the capsules obtained in the preparation described in Example 1 were used, and were identified as the "test product", along with a composition without probiotics, which was prepared in exactly the same way as that described in Example 1, but disregarding the step of adding *Lactobacillus acidophilus* and *Lactobacillus casei*; this composition was identified as the "reference product".

The total content of two capsules of the "test product", equivalent to the recommended daily dose, was dissolved in 900 mL of a culture medium known as broth M.R.S., which promotes growth of *lactobacillus*. The 900 mL of the medium are equivalent to the average volume of an adult's stomach. The final solution obtained was named as the "test solution".

The above procedure was repeated for the "reference product", thereby obtaining 900 mL of the "reference solution"

Six standard Franz diffusion cells were used. The dimensions for all cells were identical. The donor chamber had a nominal volume of 1 mL, whereas the receiving chamber having a nominal volume of 5 mL. The actual diffusion area was 0.636 cm$^2$. Both stirring and temperature of the cells were monitored throughout the experiment, and they were kept identical in each of the six cells.

The study was carried out using pig bowel as the membrane. The bowel was stored at freezing temperature (−10° C. to −15° C.) since the time of slaughter. Twenty four hours before the test, the bowel was removed from the freezer and thawed at room temperature. Once thawed, it was cleaned with water and dried with an absorbent towel. Using a scalpel, six slices of the intestinal tissue of the same thickness, approximately 1.5 mm, were obtained, and cut into 2 cm×2 cm squares.

The tissue slices were hydrated during 12 hours in phosphate buffer, pH 7.4, under refrigeration (2° C. to 8° C.). Then, they were placed into the cell containing the receiving medium, ensuring that no bubbles were present in the medium-membrane interface. Phosphate buffer, pH 6, was used as the receiving medium, simulating the achlorhydria condition typically found in patients under prolonged PPI treatments.

The experiment was performed with six cells. The donor chambers for 3 of the 6 cells were fed each with 1 mL of the "test solution", whereas the remaining three were fed each with 1 mL of the "reference solution".

The temperature of all six cells remained constant during the entire experiment by recirculating water from a thermostat bath at 35° C.-37° C. through a heating jacket.

After 48 hours of the experiment, cells were dismantled and the 6 receiving chambers were sampled. Six samples were analyzed for their content of calcium, magnesium, and iron by the atomic absorption method, and for their content of vitamin B12 by the method of the US Pharmacopoeia.

The amounts found in the receiving chamber for each of the four nutrients analyzed, were expressed as percentage (%) of the total amount added of each into the donor chamber. The results were plotted and a comparison between the "sample solution" and the "reference solution" was made.

For the four nutrients analyzed, namely calcium, magnesium, iron, and vitamin B12, the fraction of the total amount added into the donor chamber that passed through the membrane and was able to reach the receiving medium, was greater for the composition containing probiotics, this is the "test solution", in comparison to the composition without probiotics, this is the "reference solution". FIG. 1.

These results suggest that, under achlorhydria, which is precisely the condition found in patients using PPIs for prolonged periods, the addition of probiotics besides exerting its protective effect against the development of pathogenic microorganisms in the gastrointestinal tract, promotes the absorption of the four specific nutrients, whose absorption process is especially affected.

A greater absorption means less risk of causing deficiencies in the levels of these four nutrients, which in turn means less risk of adverse effects associated with these deficiencies.

Although the present invention has been described with the preferred embodiments shown, modifications and variations keeping the spirit and scope of this invention should to be considered as within the scope of the attached claims.

What is claimed is:

1. A pharmaceutical composition, comprising:
   an absorption ready vitamin;
   an absorption ready mineral;
   a probiotic comprising a 50:50 mixture of *Lactobacillus acidophilus* and *Lactobacillus casei*; and
   a prebiotic comprising a 50:50 mixture of FOS (fructooligosaccharides) and inulin.

2. The pharmaceutical composition of claim 1, wherein the vitamin is selected from the group consisting of vitamin D, vitamin K, Vitamin B12, and mixtures thereof.

3. The pharmaceutical composition of claim 2, wherein vitamin D is selected from the group consisting of calciferol, cholecalciferol, ergocalciferol, and mixtures thereof.

4. The pharmaceutical composition of claim 2, wherein the vitamin K is selected from the group comprising of menaquinone-7, menaquinone-4, and mixtures thereof.

5. The pharmaceutical composition of claim 2, wherein the vitamin B12 is selected from the group comprising of methylcobalamin, cyanocobalamin, hydroxocobalamin, and mixtures thereof.

6. The pharmaceutical composition of claim 1, wherein the absorption ready mineral is selected from the group consisting of a calcium salt, an iron salt, and mixtures thereof.

7. The pharmaceutical composition of claim 6, wherein the calcium salt is calcium citrate malate.

8. The pharmaceutical composition of claim 6, wherein the iron salt is ferrous bisglycinate.

9. The pharmaceutical composition of claim 1, further comprising a probiotic selected from the group comprising of *Bacillus clausi, Bacillus coagulans, Lactobacillus brevis, Lactobacillus vulgaricus, Lactobacillus rhamnosus, Lactobacillus helveticus, Lactobacillus lactis, Lactobacillus reuteri, Bifidobacterium bifidum, Streptococcus thermophiles, Enterococcus faecium*, and mixtures thereof.

10. The pharmaceutical composition of claim 1, wherein:
    a first vitamin is present in an amount of 5 µg to 25 µg, equivalent to 200 IU to 1,000 IU;
    a second vitamin is present in an amount of 25 µg to 200 µg;
    a third vitamin is present in an amount of 6 µg to 250 µg;
    a calcium salt present in an amount of 837 mg to 4,183 mg, equivalent to 200 mg to 1,000 mg of elemental calcium;
    an iron salt in an amount of 30 mg to 450 mg, equivalent to 6 mg to 90 mg of elemental iron;
    a first probiotic in a concentration of 1 billion CFU to 10 billion CFU;
    a second probiotic in a concentration of 1 billion CFU to 10 billion CFU;
    a first prebiotic; and
    a second prebiotic.

11. The pharmaceutical composition of claim 10, wherein:
    the first vitamin is vitamin D3, as cholecalciferol, present in an amount of 10 to 20 µg, equivalent to 400 IU to 800 IU;
    the second vitamin is vitamin K2, as menaquinone-7, present in an amount of 50 µg to 100 µg;
    the third vitamin is vitamin B12, as methylcobalamin, in an amount of 50 µg to 100 µg;
    calcium is present as calcium citrate malate, present in an amount of 1,046 mg to 2,092 mg, equivalent to 250 mg to 500 mg of elemental calcium;
    iron is present as ferrous bisglycinate, present in an amount of 90 mg to 225 mg, equivalent to 18 mg to 45 mg of elemental iron;
    the first probiotic is *Lactobacillus acidophilus*, present in an amount of 2.5 billion CFU to 7.5 billion CFU;
    the second probiotic is *Lactobacillus casei*, present in an amount of 2.5 billion CFU to 7.5 billion CFU;
    the first prebiotic FOS (fructooligosaccharides), in an amount of 25 mg to 500 mg FOS (fructooligosaccharides); and
    the second prebiotic is an inulin in an amount of between 25 mg to 500 mg.

12. The pharmaceutical composition of claim 11, wherein the first prebiotic FOS (fructooligosaccharides) is present in an amount of 50 mg to 200 mg.

13. The pharmaceutical composition of claim 1, comprising an excipient.

14. The pharmaceutical composition of claim 13, wherein the excipient is selected from the group consisting of a diluent, a disintegrant, a glidant, a lubricant, and mixtures thereof.

15. The pharmaceutical composition of claim 14, further comprising:
    a diluent in a concentration of 5% to 20% of the total weight of the preparation;
    a disintegrant in a concentration of 0.5% to 5% of the total weight of the preparation;

a glidant in a concentration of 0.5% to 5% of the total weight of the preparation; and a lubricant in a concentration of 0.5% to 3% of the total weight of the preparation.

16. A method of treatment to avoid adverse effects associated with the use of proton-pump inhibitors, comprising: oral administration of the pharmaceutical composition of claim 1.

17. The method of treatment to avoid adverse effects associated with the use of proton-pump inhibitors of claim 16, wherein: the absorption ready vitamin includes cholecalciferol from 10 µg and 20 µg, equivalent to 400 IU and 800 IU of vitamin D3; menaquinone-7 from 50 µg to 100 µg; methylcobalamin from 50 µg to 100 µg;

the absorption ready mineral includes calcium citrate malate from 1,046 mg to 2,092 mg, equivalent to 250 mg to 500 mg of elemental calcium; magnesium oxide from 166 mg to 664 mg, equivalent to 100 mg to 400 mg of elemental magnesium; ferrous bisglycinate from 90 mg to 225 mg, equivalent to 18 mg to 45 mg of elemental iron;

the probiotic includes *Lactobacillus acidophilus* from 2.5 billion CFU to 7.5 billion CFU and *Lactobacillus casei* from 2.5 billion CFU to 7.5 billion CFU; and the prebiotic includes FOS (fructooligosaccharides) from 50 mg to 200 mg and inulin from 50 mg to 200 mg.

18. The method of treatment of claim 16, wherein the pharmaceutical composition is administered from 4 to 6 hours after the first daily administration of the proton-pump inhibitor.

19. The method of claim 18, wherein the pharmaceutical composition is administered in two capsules or tablets, each one containing half the total daily dose required.

20. A method of preparation of a pharmaceutical composition that prevents adverse effects associated with the use of proton-pump inhibitors, comprising:

sifting Vitamins D3, K2, and B12 and colloidal silicon dioxide through a #100 mesh;

geometrically diluting the vitamins D3, K2 and B12 in colloidal silicon dioxide and mixing for 5 minutes at each dilution to obtain a geometrically diluted pre-mix;

sifting microcrystalline cellulose through a #30 mesh;

geometrically diluting the obtained pre-mix in microcrystalline cellulose, mixing for 5 minutes at each dilution to obtain a pre-mix which is added to a mixer and mixed for 10 minutes;

separately, *Lactobacillus acidophilus, Lactobacillus casei*, FOS (fructooligosaccharides), and inulin are mixed for 5 minutes after being previously sifted through a #30 mesh to obtain a pre-mix which is added to a mixer and mixed for 10 minutes;

separately, iron bisglycinate, magnesium oxide, and sodium croscarmellose are mixed for 5 minutes after being previously sifted through a #30 mesh to obtain a pre-mix which is added to a mixer and mixed for 10 minutes;

calcium citrate malate is placed in a "V" mixer after being previously sifted through a #20 mesh;

vegetable magnesium stearate, previously sifted through a #60 mesh, is added to the mixer and mixed for 3 minutes, which yields a pharmaceutical composition comprising;

an absorption ready vitamin;

an absorption ready mineral;

a probiotic comprising a 50:50 mixture of *Lactobacillus acidophilus* and *Lactobacillus casei*; and a prebiotic comprising a 50:50 mixture of FOS (fructooligosaccharides) and inulin.

21. The method of claim 20, wherein a "#00" capsule is filled with an average weight of 850 mg of the pharmaceutical composition.

22. A pharmaceutical composition, comprising:

an absorption ready vitamin; wherein a first vitamin is present in an amount of 5 µg to 25 µg, equivalent to 200 IU to 1,000 IU;

a second vitamin is present in an amount of 25 µg to 200 µg;

a third vitamin is present in an amount of 6 µg to 250 µg;

an absorption ready mineral; wherein said absorption ready mineral is at least one of a calcium salt or an iron salt and wherein the calcium salt present in an amount of 837 mg to 4,183 mg, equivalent to 200 mg to 1,000 mg of elemental calcium;

the iron salt in an amount of 30 mg to 450 mg, equivalent to 6 mg to 90 mg of elemental iron;

a first probiotic in a concentration of 1 billion CFU to 10 billion CFU;

a second probiotic in a concentration of 1 billion CFU to 10 billion CFU; and a prebiotic.

23. The pharmaceutical composition of claim 22, wherein:

the first vitamin is vitamin D3, as cholecalciferol, present in an amount of 10 µg to 20 µg, equivalent to 400 IU to 800 IU;

the second vitamin is vitamin K2, as menaquinone-7, present in an amount of 50 µg to 100 µg;

the third vitamin is vitamin B12, as methylcobalamin, in an amount of 50 µg to 100 µg;

calcium is present as calcium citrate malate, present in an amount of 1,046 mg to 2,092 mg, equivalent to 250 mg to 500 mg of elemental calcium;

iron is present as ferrous bisglycinate, present in an amount of 90 mg to 225 mg, equivalent to 18 mg to 45 mg of elemental iron;

the first probiotic is *Lactobacillus acidophilus*, present in an amount of 2.5 billion CFU to 7.5 billion CFU;

the second probiotic is *Lactobacillus casei*, present in an amount of 2.5 billion CFU to 7.5 billion CFU;

the first prebiotic FOS (fructooligosaccharides), in an amount of 25 mg to 500 mg FOS (fructooligosaccharides), present in an amount of 50 mg to 200 mg; and the second prebiotic is an inulin in an amount of between 25 mg to 500 mg.

* * * * *